US00RE36120E

United States Patent [19]

Karell

[11] E Patent Number: Re. 36,120

[45] Reissued Date of Patent: Mar. 2, 1999

[54] SNOPPER—THE SNORING STOPPER ANTI-SNORING MOUTH DEVICE

[76] Inventor: Manuel L. Karell, 3573-22nd St., San Francisco, Calif. 94114

[21] Appl. No.: 598,203

[22] Filed: Feb. 7, 1996

Related U.S. Patent Documents

Reissue of:

[64] Patent No.: 5,284,161
Issued: Feb. 8, 1994
Appl. No.: 975,425
Filed: Nov. 12, 1992

[51] Int. Cl.[6] ..... A61F 5/56

[52] U.S. Cl. ..... 128/848; 600/554; 607/134

[58] Field of Search ..... 607/42, 44, 118, 607/134, 5; 128/741, 848

[56] References Cited

U.S. PATENT DOCUMENTS

| | | | |
|---|---|---|---|
| 3,480,010 | 11/1969 | Crossley | 128/132 |
| 3,522,811 | 8/1970 | Schwartz et al. | 607/44 |
| 4,153,060 | 5/1979 | Korostoff et al. | 607/51 |
| 4,310,002 | 1/1982 | Takinishi et al. . | |
| 4,519,400 | 5/1985 | Brenman et al. | 128/741 |
| 4,637,405 | 1/1987 | Brenman et al. | 607/134 |
| 4,644,330 | 2/1987 | Dowling | 340/575 |
| 4,669,459 | 6/1987 | Spiewak et al. | 128/136 |
| 4,715,367 | 12/1987 | Crossley . | |
| 4,788,533 | 11/1988 | Mequignon | 340/575 |
| 4,830,008 | 5/1989 | Meer . | |
| 4,901,737 | 2/1990 | Toone | 128/848 |
| 4,907,602 | 3/1990 | Sanders | 607/134 |
| 4,924,880 | 5/1990 | O'Neill et al. | 607/134 |
| 4,944,310 | 7/1990 | Sullivan | 128/848 |
| 5,042,506 | 8/1991 | Liberati | 128/848 |
| 5,123,425 | 6/1992 | Shannon, Jr. et al. . | |
| 5,146,918 | 9/1992 | Kallok et al. | 607/42 |
| 5,178,156 | 1/1993 | Takishimi et al. | 607/42 |
| 5,190,053 | 3/1993 | Meer | 607/134 |
| 5,207,231 | 5/1993 | Fakhri | 607/134 |
| 5,330,527 | 7/1994 | Montecalvo et al. . | |
| 5,427,096 | 6/1995 | Bogusiewicz et al. . | |
| 5,591,216 | 1/1997 | Testerman et al. . | |

FOREIGN PATENT DOCUMENTS

| | | | |
|---|---|---|---|
| 1553140 | 3/1990 | U.S.S.R. | 128/787 |
| 5005278 | 12/1985 | WIPO | 607/134 |

OTHER PUBLICATIONS

Herbert Paskow and Sanford Paskow, "Dentistry's Role in Treating Sleep Apnea and Snoring," New Jersey Medicine, vol. 88, No. 11, Nov. 1991, pp. 815–817.

*Primary Examiner*—William E. Kamm
*Attorney, Agent, or Firm*—Reed Smith Shaw & McClay

[57] ABSTRACT

A novel medical device, SNOPPER—The Snoring Stopper™ anti-snoring mouth device, is inserted into the mouth. The device comprises a denture-like(10) apparatus for supporting electrodes(12) in such a manner that the electrodes make contact with the roof of the mouth. Electrical stimulation induces contraction of relaxed muscles, thereby preventing or stopping snoring. Electrical energy is provided to the device via wires for connection to an external stimulator (16) or via a self-contained, battery-powered, microminiaturized electronic stimulator(20). Stimulation can be constant or intermittent. Wave shape, [amplitutde] *amplitude*, length, and frequency is controlled by the individual for comfort and is automatically induced via a feedback mechanism.

11 Claims, 3 Drawing Sheets

SNOPPER— THE SNORING STOPPER ANTI-SNORING MOUTH DEVICE

Matter enclosed in heavy brackets [ ] appears in the original patent but forms no part of this reissue specification; matter printed in italics indicates the additions made by reissue.

BACKGROUND

1. Field of Invention

This invention generally relates to medical devices, and more particularly to a novel device inserted into the mouth to prevent or stop snoring.

2. Description of Prior Art

Snoring, *including the most severe forms of snoring such as obstructive sleep apnea,* is caused, in part, by relaxation of muscles during respiration while asleep. Various devices have been introduced to alleviate snoring. One device (U.S. Pat. No. 4,669,459 to Spiewak, 1987) provides pressure to the muscles, and another (U.S. Pat. No. 4,901,737 to Toone, 1990) provides an open mouth position. Other devices attempt to keep the tongue protruded, for example, the Samelson and Gardy devices, NJ Medicine, Vol. 88 No. 11 Nov. 1991. Still other devices (such as U.S. Pat. No. 4,644,330 to Dowling, 1987 and U.S. Pat. No. 4,788,533 to Mequignon, 1988) attempt to stop snoring by sound feedback. One device, U.S. Pat. No. 3,480,010 to Crossley, 1969) provides electrodes that attach to the skin of the neck via a neck band to shock the sleeper and condition him against snoring. One device, (U.S. Pat. No. 5,042,506 to Liberati, 1991) attempts to train the muscles to prevent snoring. Continuous positive air pressure breathing devices (U.S. Pat. No. 4,944,310 to Sullivan, 1990) and surgery are currently used to treat severe snoring and obstructive sleep apnea.

OBJECTS AND ADVANTAGES

SNOPPER—The Snoring Stopper™ anti-snoring mouth device provides electrical stimulation to the muscles of the mouth, from inside the mouth, to induce contraction and tension of relaxed muscles, thereby eliminating snoring.

SNOPPER—The Snoring Stopper™ anti-snoring mouth device allows for direct action to the muscles. There is no need for retraining of muscles, sound feedback, sleep interruption, or abnormal mouth positions or tongue protrusion positions.

SNOPPER—The Snoring Stopper™ anti-snoring mouth device obviates the need for continuous positive air pressure breathing devices or surgery.

SNOPPER—The Snoring Stopper™ anti-snoring mouth device can be configured as a self-contained battery-powered system that delivers electrical stimulation that can be adjusted for individual comfort.

DESCRIPTION OF FIGS. 1–3

Figure 1:
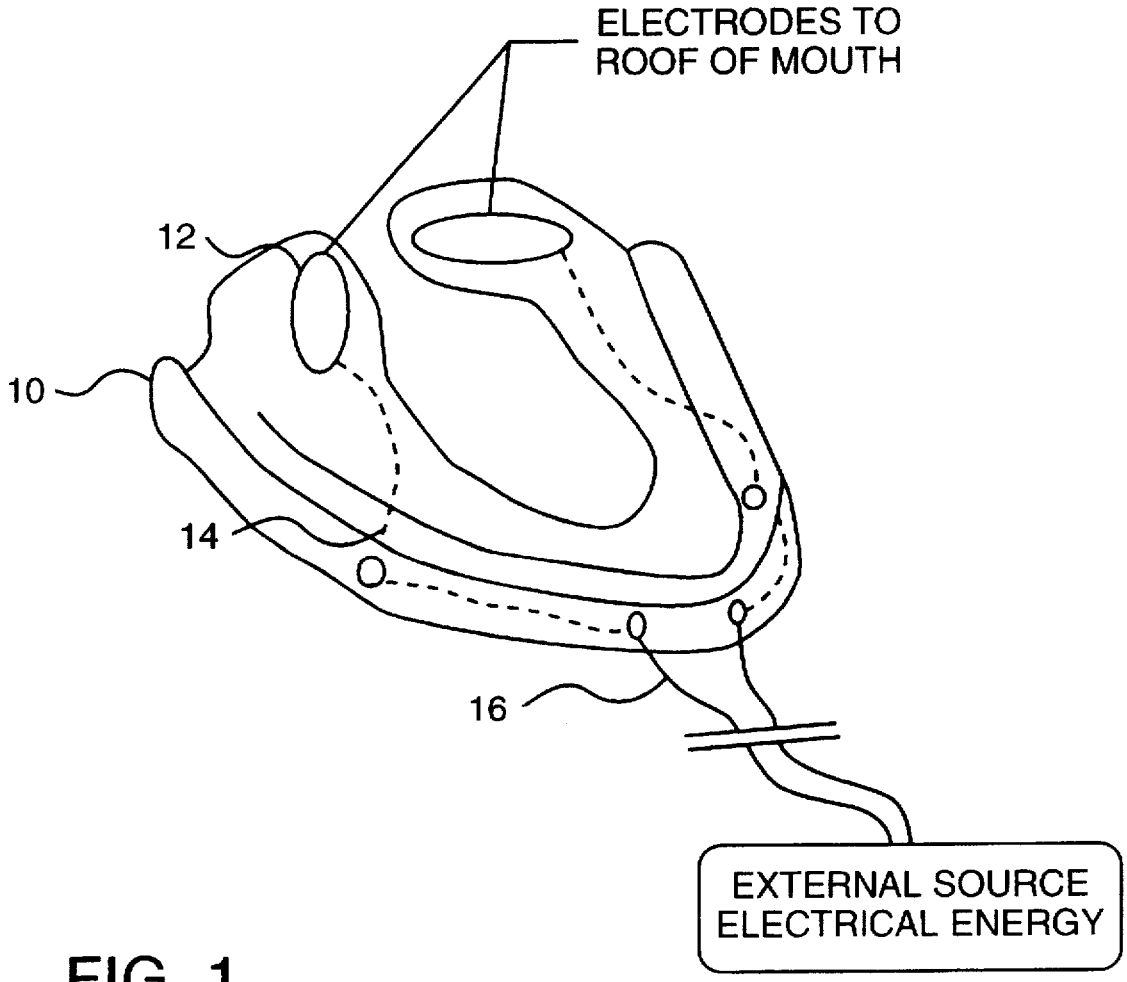
FIG. 1 is a perspective drawing of a SNOPPER—The Snoring Stopper™ anti-snoring mouth device.
Figure 2:
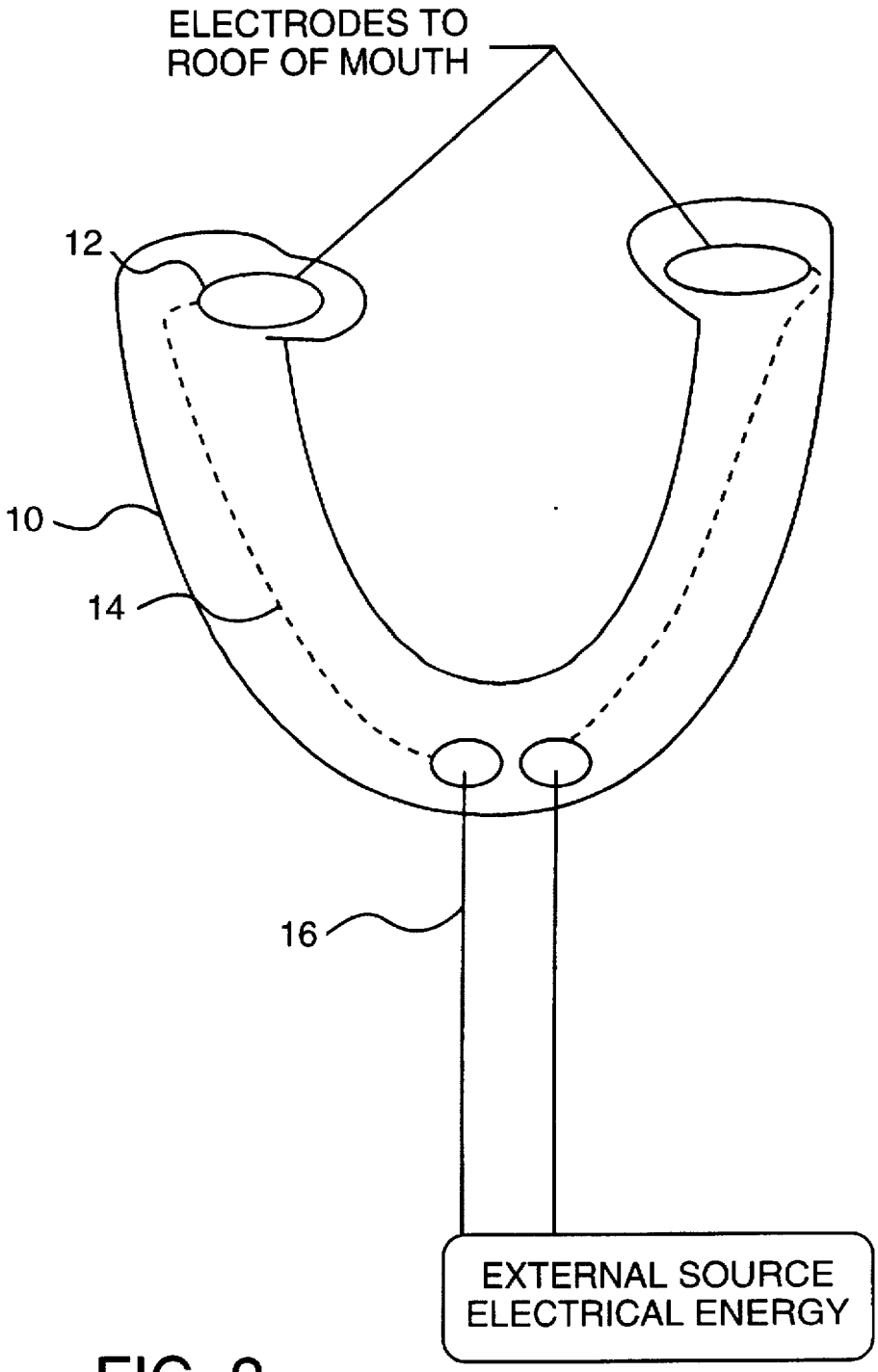
FIG. 2 is a plan view drawing of SNOPPER—The Snoring Stopper™ anti-snoring mouth device.

A typical embodiment of my invention SNOPPER—The Snoring Stopper™ anti-snoring mouth device is illustrated in FIG. 1 (perspective view) and FIG. 2 (plan view). Electrodes(12), which are supported by a molded denture-like device(10), make contact with the roof of the mouth, *e.g., the hard palate, soft palate or upper nasal oral pharynx. The electrodes can be made of any conventional electroconductive material, including electroconductive rubber.* The electrodes(12) are connected to internal wires(14), which are connected to external wires(16). The external wires(16) are connected to an external source of energy(18).

Figure 3:
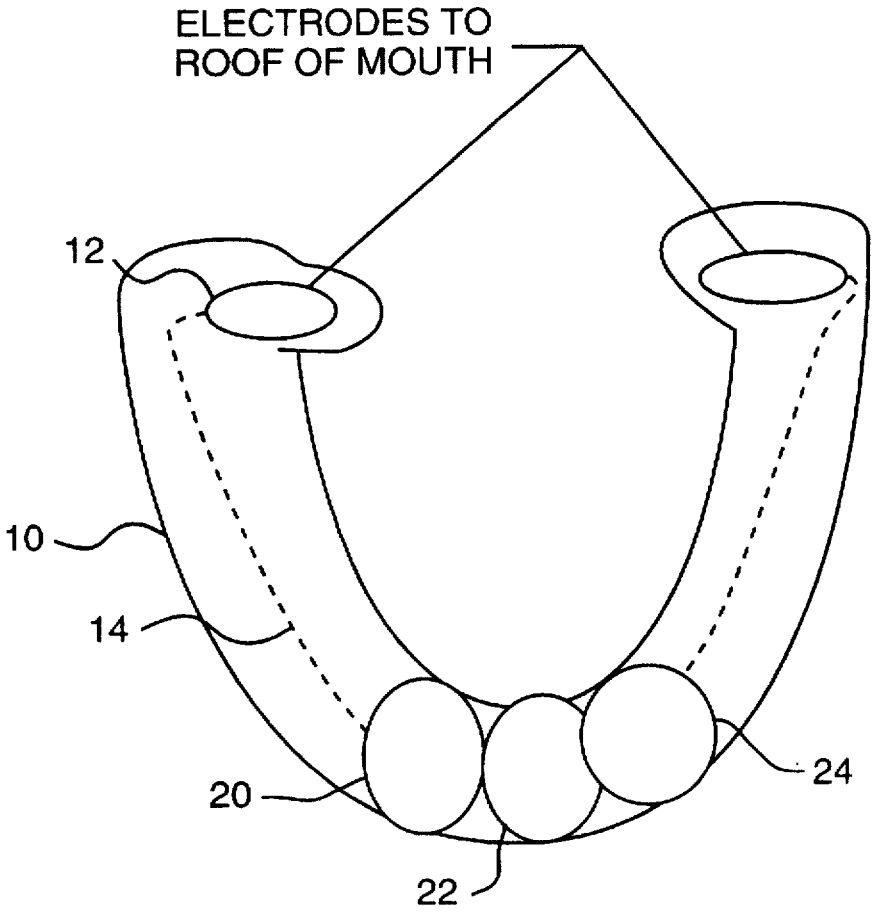
FIG. 3 is a plan view of an embodiment of SNOPPER—The Snoring Stopper™ anti-snoring mouth device with *a* self-contained, battery-powered, microminiaturized electronic stimulator.

The plan view in FIG. 3 shows the device(10) alternatively constructed so that the internal wires(14)[.] are in turn connected to a battery-powered(24), switched(22), microminiaturized electronic stimulator unit(20).

OPERATION OF INVENTION

It is believed that snoring is caused, in part, by the relaxation of muscles during respiration while asleep. My SNOPPER—The Snoring Stopper™ anti-snoring mouth device[.] provides energized electrodes for delivering electrical stimulation. This stimulation induces contraction and tension of relaxed muscles thereby preventing or stopping snoring.

Electrical energy(18) is delivered to device(10) via external wires(16), transferred via internal wires(14) to electrodes (12). The energized electrodes induce contraction of muscles. Also, the electrical stimulation can induce rhythmic contraction waves that interfere with snoring rhythms. The device can be configured with a feedback mechanism (not shown) whereby snoring causes the onset of electrical stimulation.

Electrical energy can be provided via commercial transcutaneous electric nerve stimulator units (such as U.S. Pat. No. 4,949,721 to Toriu, 1990, or, U.S. Pat. No. 5,072,710 to Lee, 1991) attached to the wires(16). Alternatively, electrical energy can be provided via self-contained, battery-powered, microminiaturized stimulator units within SNOPPER—The Snoring Stopper™ anti-snoring mouth device (FIG. 3); in this case, the device user controls and adjusts wave shape, amplitude, length, and frequency of the electrical stimulation, which can be intermittent or constant.

SUMMARY

SNOPPER—The Snoring Stopper™ anti-snoring mouth device with built-in electrodes is inserted into the mouth for electromuscular stimulation, inducing muscle contraction and tension, thereby preventing or stopping snoring. Electrical stimulation can be provided via connections to *an* external source or via a self-contained, battery-powered, microminiaturized electronic unit. Electrical stimulation can be constant or intermittent, using *any of* a variety of wave forms, [amplitude] *amplitudes*, [length] *lengths*, and [frequency] *frequencies* as required for individual comfort. The device itself and its electrodes can be made in a variety of shapes and *with a variety of* materials.

Conclusions, Ramifications and Scope of Invention

The novel use of electrodes within a denture-like plate or other apparatus makes a SNOPPER—The Snoring Stopper™ anti-snoring mouth device beneficial. While the above description contains many specificities, these should not be construed as limitations on the scope of the invention, but rather as an exemplification of two preferred embodiments thereof. Many other variations are possible. For example, electrodes could be installed permanently through or between the teeth, or stimulation in this area can be prolonged to induce a beneficial long term hypotensive response. Accordingly, the scope of the invention should be determined not by the embodiments illustrated, but by the appended claims and their legal equivalents.

I claim:

[1. An apparatus for the cessation of snoring, wherein said apparatus comprises:

mouthpiece means for fitting over an entire upper tooth plate in a person's mouth and providing surfaces for contacting a upper mouth roof;

electrode means, implanted within said mouthpiece means, for ceasing snoring through an application of electrical energy to the upper mouth roof; and energy means for supplying electrical energy to said electrode means.]

[2. An apparatus of claim 1, wherein said energy means is a microminiaturized stimulation unit implanted within said mouthpiece.]

[3. An apparatus of claim 1, wherein said electrode means is constructed of a soft, pliable, electroconductive rubber-like material.]

[4. An apparatus of claim 1, wherein said energy means comprises:

internal wires implanted within said mouthpiece;

external wires connected to said internal wires; and an external energy source connected to said external wires.]

*5. An electromuscular stimulator for providing electrical stimulation to the muscles of the mouth of a patient to induce tension and contraction of relaxed muscles comprising:*

*positioning means for insertion in the patient's mouth and providing surfaces for contacting a mouth roof;*

*electrode means, disposed on said positioning means, for making electrical contact with the mouth roof; and*

*energy means for supplying electrical energy to said electrode means.*

*6. The electromuscular stimulator of claim 5, wherein said positioning means includes means for fitting over at least a portion of a tooth plate.*

*7. The electromuscular stimulator of claim 5, wherein said positioning means includes means for fitting over an entire tooth plate.*

*8. The electromuscular stimulator of claim 5, wherein said positioning means includes means for fitting over at least a portion of an upper tooth plate.*

*9. The electromuscular stimulator of claim 5, wherein said positioning means includes means for fitting over an entire upper tooth place.*

*10. The electromuscular stimulator of claim 5, wherein said energy means is a microminiaturized stimulation unit implanted within said positioning means.*

*11. The electromuscular stimulator of claim 10, further comprising a battery for powering said microminiaturized stimulation unit.*

*12. The electromuscular stimulator of claim 5, wherein said electrode means comprises an electroconductive rubber-like material.*

*13. The electromuscular stimulator of claim 5, wherein said energy means comprises:*

*at least one internal wire implanted within said positioning means;*

*at least one external wire connected to said at least one internal wire; and*

*an external energy source connected to said at least one external wire.*

*14. The electromuscular stimulator of claim 5, wherein the positioning means comprises a denture-like plate.*

*15. The electromuscular stimulator of claim 5, wherein the positioning means comprises a molded device.*

* * * * *